(12) United States Patent
Qi et al.

(10) Patent No.: US 7,919,656 B2
(45) Date of Patent: Apr. 5, 2011

(54) LINEAR AMINE FUNCTIONALIZED POLY(TRIMETHYLENE ETHER) COMPOSITIONS

(75) Inventors: Kai Qi, Wilmington, DE (US); Hari Babu Sunkara, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/704,867

(22) Filed: Feb. 12, 2010

(65) Prior Publication Data
US 2010/0160573 A1    Jun. 24, 2010

Related U.S. Application Data

(62) Division of application No. 12/342,334, filed on Dec. 23, 2008, now Pat. No. 7,728,175.

(51) Int. Cl.
| | | |
|---|---|---|
| C07C 217/42 | (2006.01) | |
| C07C 209/08 | (2006.01) | |
| C07C 209/22 | (2006.01) | |
| C07C 209/48 | (2006.01) | |

(52) U.S. Cl. ........ 564/511; 564/474; 564/491; 564/497; 564/498

(58) Field of Classification Search ............... None
See application file for complete search history.

(56) References Cited

U.S. PATENT DOCUMENTS

| | | | |
|---|---|---|---|
| 3,236,895 A | 2/1966 | Lee et al. | |
| 3,532,653 A * | 10/1970 | Smeal | 523/450 |
| 3,654,370 A | 4/1972 | Yeakey | |
| 3,666,788 A | 5/1972 | Rowton | |
| 3,773,703 A * | 11/1973 | Smeal | 523/417 |
| 3,979,364 A | 9/1976 | Rowton | |
| 4,036,881 A | 7/1977 | Brennan et al. | |
| 4,122,069 A | 10/1978 | Meyer | |
| 4,178,427 A | 12/1979 | Waddill et al. | |
| 4,689,131 A | 8/1987 | Roue et al. | |
| 4,914,072 A | 4/1990 | Grice et al. | |
| 5,874,623 A * | 2/1999 | Adkins et al. | 564/474 |
| 5,990,237 A | 11/1999 | Bentley et al. | |
| 6,294,697 B1 * | 9/2001 | Wilbur et al. | 564/505 |
| 6,362,254 B2 | 3/2002 | Harris et al. | |
| 6,492,560 B2 * | 12/2002 | Wilbur et al. | 564/505 |
| 2005/0234216 A1 | 10/2005 | Klein et al. | |
| 2007/0173669 A1 | 7/2007 | Sunkara et al. | |
| 2007/0249870 A1 | 10/2007 | Chenault | |
| 2008/0004421 A1 | 1/2008 | Chenault et al. | |

OTHER PUBLICATIONS

International Search Report, PCT International Application PCT/US2009/062286, Mailed Apr. 12, 2010.
A. X. Swamikannu et al., Preparation and Characterization of P-Toluene Sulfonyl Ester and Amino Derivatives of Tri- and Poly(Ethylene Glycol), J. of Polymer Science: Polymer Chemistry Edition, 22 (1984), pp. 1623-1632.
J. G. Schmidt et al., Synthesis of Orthogonal End Functionalized Oligoethylene Glycols of Defined Length, Tetrahedron Letters, 45 (2004) pp. 4285-4288.
E. Schacht et al., End-Group Modification of Alpha-Hydro-Omega-Methoxypoly(Oxy-Ethylene), 2 A), Facile Methods for the Introduction of an Alpha-Amino End-Group, Makromol. Chem., Rapid Commun., 12 (1991), pp. 159-165.
B. Pfannemuller et al., Linear and Star-Shaped Hydrbid Polymers, 2 A), Coupling of Mono- and Oligosaccharides to Alpha, Omega-Diamino Substituted Poly(Oxyethylene) and Multifunctional Amines by Amide Linkage, Makromol. Chem., Rapid Commun., 5 (1984), pp. 373-379.
B. Pfannemuller et al., Linear and Star-Shaped Hydrbid Polymers, 1, A New Method for the Conversion of Hydroxyl End Groups of Poly(Oxyethylene) and Other Polyolds Into Amino End Groups, Makromol. Chem., Rapid Commun., 5 (1984), pp. 363-371.
M. Mutter, Soluble Polymers in Organic Synthesis: I. Preparation of Polymer Reagents Using Polyethylene Glycol With Terminal Amino Groups As Polymeric Component, Tetrahedron Letters, No. 31 (1971), pp. 2839-2842.
M. Morr et al., Functionalization of Poly(Ethylene Glycol) and Monomethoxy-Poly (Ethylene Glycol), Makromol. Chem. 182 (1981), pp. 1379-1384.
S. P. McManus et al., Chain-Cleavage and Hydrolysis of Activated Polyethylene Glycol Derivatives: Evidence for Competitive Processes, J. Polymer Science: Part A: Polymer Chemistry, 28 (1990), pp. 3337-3346.
J. M. Harris, Laboratory Synthesis of Polyethylene Glycol Derivatives, JMS-Rev. Macromol. Chem. Phys., C25 (3) (1985), pp. 325-373.
J. M. Harris et al., Synthesis and Characterization of Poly(Ethylene Glycol) Derivatives, J. Polymer Science: Polymer Chemistry Edition, 22 (1984), pp. 341-352.
E. J. Goethals et al., Conventient Synthesis of Alpha-Tosyl-Omega-Tosyloxypoly (Oxythylene), Makromol. Chem., Rapid Commun., 6 (1985), pp. 53-56.
E. Dellacherie et al., Synthesis and Characterization of a Polyoxyethylene Derivative for the Affinity Labeling of Human Hemoglobin, Makromol. Chem., 189 (1988), pp. 1809-1817.
M. B. Andrus et al., Synthesis and Analysis of Polyethylene Glycol Linked P-Glycoprotein-Specific Homodimers Based on (−)-Stipiamide, Tetrahedron Letters 42 (2001), pp. 3819-3822.
S. Zalipsky, Functional Poly(Ethylene Glycol) for Preparation of Biologically Relevant Conjugates, Bioconjugate Chem., 6 (1985), pp. 150-165.

* cited by examiner

Primary Examiner — Brian J Davis
(74) Attorney, Agent, or Firm — Gail D. Tanzer

(57) ABSTRACT

The present invention relates to linear amine-functionalized poly(trimethylene ether) compositions, and processes to produce these compositions.

7 Claims, No Drawings

LINEAR AMINE FUNCTIONALIZED POLY(TRIMETHYLENE ETHER) COMPOSITIONS

FIELD OF THE INVENTION

The present invention relates to linear amine-functionalized poly(trimethylene ether) compositions, and processes for producing the compositions.

BACKGROUND

Poly(trimethylene ether)glycol is widely used as an intermediate in thermoplastic elastomers. Processes for preparing polyoxyalkylene polyamines using polyoxyalkylene glycols with ammonia and hydrogen in the presence of Raney nickel catalysts are disclosed in U.S. Pat. No. 3,236,895. Poly(ethylene glycol) derivatives also reported by J. Milton Harris (J. Macromolecular Science Reviews in Macromolecular Chemistry, 1985, vol C-25, No. 3, P325-373).

Poly(trimethylene ether)amines are useful in a variety of applications such as chain extenders for polyurethane urea polymers, curing agents for epoxy resins, polyurethane coatings, components for making polyamides, initiators for the preparation of polyols, or health care product additives.

SUMMARY OF THE INVENTION

One aspect of the present invention is a poly(trimethylene ether)diamine compound of the formula

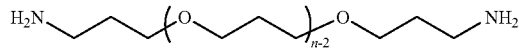

wherein n is 4 to 170, preferably 4 to 100.

Another aspect of the present invention is a process for making a poly(trimethylene ether)diamine of the formula

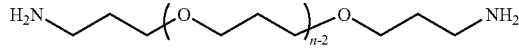

wherein n is 4 to 170, preferably 4 to 100, comprising:
a) contacting poly(trimethylene ether)glycol of the formula

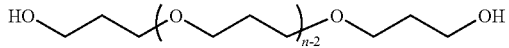

with thionyl halide and optionally with dimethylformamide, optionally in the presence of a solvent, at a temperature less than about 25° C., to form a reaction mixture;
b) raising the temperature of the reaction mixture to a temperature of 50 to 150° C. and holding the reaction mixture at the raised temperature for about 2 to 24 hours;
c) allowing the formation of a poly(trimethylene ether)halide of the formula

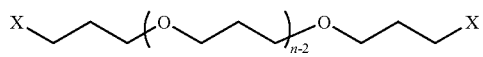

wherein X is Cl or Br;

d) combining the poly(trimethylene ether)halide with 1-10 molar equivalents of alkali metal azide in the presence of a solvent at a temperature of 25 to 200° C. to form a poly(trimethylene ether)azide of the formula

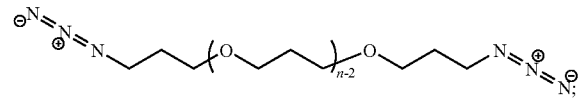

and
e) contacting the poly(trimethylene ether)azide with a reducing agent, or under hydrogen gas with catalytic amount of catalyst, in a solvent or solvent mixture, at a pressure of about 15 to 500 psi and at a temperature of 25 to 200° C., to form a poly(trimethylene ether)amine of the structure

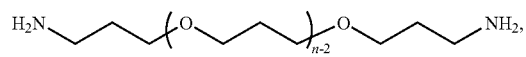

wherein n is 4 to 170, preferably 4 to 100.

A further aspect of the present invention is a process for making a poly(trimethylene ether)diamine of the formula

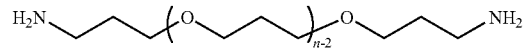

comprising:
a) providing a poly(trimethylene ether)glycol, having chain-end hydroxyl groups, of the formula

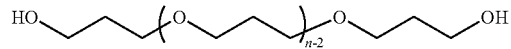

and converting the chain-end hydroxyl groups of the poly(trimethylene ether)glycol to form a compound of formula

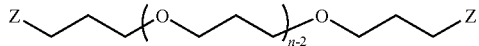

where Z is selected from the group consisting of: mesylate (—OMs), tosylate (—OTs), nosylate (—ONs), brosylate (—OBs), triflate (—OTf), nonaflate, tresylate, iodide (—I)
b) combining the compound from step (a) with 1-10 molar equivalents of alkali metal azide in the presence of a solvent at a temperature of 25 to 200° C. to form a poly(trimethylene ether)azide of the formula

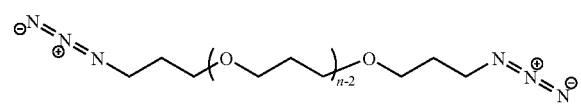

and
c) contacting the poly(trimethylene ether)azide with a reducing agent or, under hydrogen gas with catalytic amount of catalyst, in a solvent or solvent mixture, at a pressure of about 15 to 500 psi and at a temperature of 25 to 200° C., to form a poly(trimethylene ether)amine of the structure

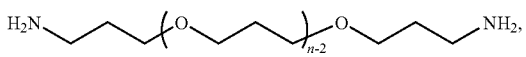

wherein n is 4 to 170, preferably 4 to 100.

Another aspect of the present invention is a process for making a poly(trimethylene ether)diamine of the formula

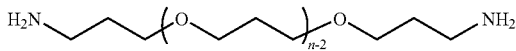

comprising:

a) contacting poly(trimethylene ether)glycol of the formula

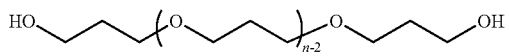

with thionyl halide and optionally with catalytic amount of dimethylformamide (DMF), optionally in the presence of a solvent, at a temperature less than about 25° C. to form a reaction mixture;

b) raising the temperature of the reaction mixture to a temperature of 50 to 150° C., and holding the reaction mixture at the raised temperature for about 2 to 24 hours to form a poly(trimethylene ether)halide of the formula:

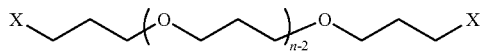

wherein X is Cl or Br;

c) contacting the poly(trimethylene ether)halide with anhydrous ammonia, or a mixture of aqueous ammonia and a suitable solvent, under a pressure of 15 to 500 psi and at a temperature of 25 to 150° C. to form a poly(trimethylene ether)diamine of the formula

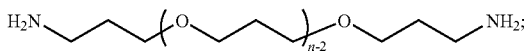

wherein n is 4 to 170, preferably 4 to 100.

A further aspect of the present invention is a process for making a poly(trimethylene ether)diamine of the formula

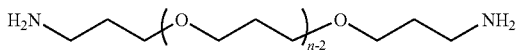

comprising:

a) converting poly(trimethylene ether)glycol of the formula

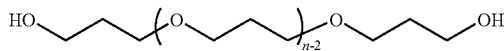

to a compound of formula

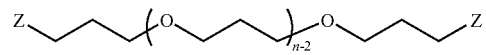

where Z is selected from the group consisting of mesylate (—OMs), tosylate (—OTs), nosylate (—ONs), brosylate (—OBs), triflate (—OTf), nonaflate, tresylate and iodide (—I);

b) combining the compound from step (a) with anhydrous ammonia or a mixture of aqueous ammonia and a suitable solvent under a pressure of about 15 to 500 psi at a temperature of 25 to 150° C. to form a poly(trimethylene ether)diamine of the formula

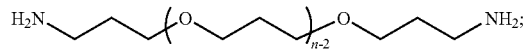

wherein n is 4 to 170, preferably 4 to 100.

Another aspect of the present invention is a process for making a poly(trimethylene ether)diamine of the formula

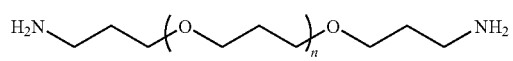

comprising:

a) providing a poly(trimethylene ether)glycol of the formula

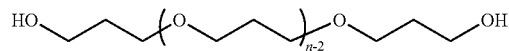

and converting the chain-end hydroxyl groups thereof to form a nitrile-terminated poly(trimethylene ether) of formula

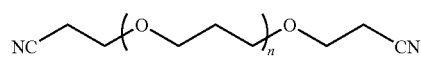

b) reducing the nitrile-terminated poly(trimethylene ether) in the presence of hydrogen and catalyst at a temperature of 50 to 250° C. under a pressure of 80 to 4000 psi to form a poly(trimethylene ether)diamine of the formula

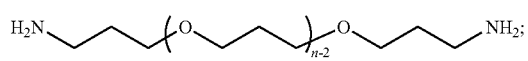

wherein n is 4 to 170, preferably 4 to 100.

These and other aspects of the present invention will be apparent to one skilled in the art in view of the present disclosure and the appended claims.

DETAILED DESCRIPTION

Unless otherwise defined, all technical and scientific terms used herein have the same meaning as commonly understood by one of ordinary skill in the art to which this invention belongs. In case of conflict, the present specification, including definitions, controls.

The present invention provides linear amine-functionalized poly(trimethylene ether) compositions, and processes to produce them.

Generally, the compositions made according to the processes disclosed herein are known as poly(trimethylene ether)diamines and have the structure

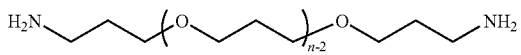

wherein n is 4 to 170, and preferably 4 to 100.

Processes disclosed herein for making the poly(trimethylene ether)diamines generally begin by contacting poly(trimethylene ether)glycol having the structure

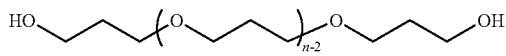

wherein n is 4 to 170, and preferably 4 to 100, with a chemical compound that will react with the glycol.

Unless stated otherwise, weight percentages given herein, particularly with respect to reactants and compounds, including catalysts, that are contacted with a poly(trimethylene ether)glycol or a compound derived therefrom, are relative to the weight of the poly(trimethylene ether)glycol compound or derived compound.

In one embodiment, the poly(trimethylene ether)glycol is reacted with thionyl chloride or thionyl bromide, optionally containing a stoichiometric amount (up to 80% by weight), or preferably a catalytic amount (0.01% to 15% by weight, preferably 0.1% to 10% by weight) of dimethyl formamide, neat or in the presence of a solvent that it is compatible with poly(trimethylene ether)glycol, at controlled temperatures, generally within the range from −78° C. to room temperature (e.g., about 25° C.), typically from about −20° C. to 10° C., more typically around 0° C.) to form a reaction mixture. Suitable compatible solvents include toluene, dichloromethane, ethyl acetate, ethyl ether, ethanol, methanol, acetone, dioxane, tetrahydrofuran hexane, and cyclohexane. The choice of solvent depends in part on the molecular weight of the poly(trimethylene ether)glycol. Polar solvents such as alcohols, esters, and ethers are generally preferred for lower molecular weight polymers, and aliphatic hydrocarbon solvents such as pentane, petroleum ether and hexane are generally preferred for higher molecular weight polymers. The temperature of the reaction mixture is then raised to a temperature of 50 to 150° C., generally 50 to 100° C., and held at the raised temperature for about 2 to about 24 hours with stirring, and a dihalide compound is thereby formed, having the structure

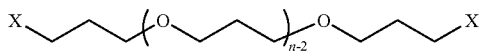

where X is Cl or Br derived from the thionyl compound with which the poly(trimethylene ether)glycol was reacted.

The resulting poly(trimethylene ether)halide is then combined with appropriate amount of alkali metal azide such as, for example, sodium azide to allow for the conversion of the halide functional groups to azide functional groups, in dimethylformamide solvent at an elevated temperature, generally 25 to 200° C., more typically 50 to 150° C.) either at atmosphere pressure or a pressure of 15 to 150 psi depending on the choice of solvent, temperature, and catalyst to form a poly(trimethylene ether)azide of the structure

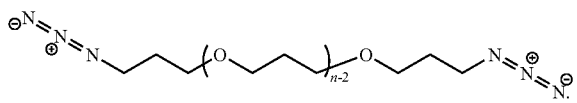

The preferred amount of alkali metal azide is 1 to 10 molar equivalents to the halide functional groups. Other solvents, preferably polar solvents, can be used for this reaction, such as, for example, water, acetone, methanol, isopropanol, N,N'-dimethylformamide (DMF), dimethylsulfoxide (DMSO), N,N'-dimethylacetamide (DMAc), N-methylpyrrolidone (NMP) and mixtures thereof.

The poly(trimethylene ether)azide is then exposed to a catalyst (generally 0.01% to 15% by weight, preferably 0.1% to 10% by weight) in the presence of hydrogen gas at ambient or elevated temperature, generally 25 to 200° C., and more typically 50 to 150° C., and at ambient pressure or elevated pressure, typically 15 to 500 psi, preferably 20 to 100 psi, to form the desired poly(trimethylene ether)amine. One suitable catalyst is palladium, 10 wt. % on activated carbon, which is available from commercial suppliers, such as Sigma-Aldrich. However, a variety of catalysts can be used, including cobalt-nickel, cobalt manganese, cobalt boride, copper cobalt, iron oxide, zinc, Raney nickel, rhodium on charcoal or alumina, rhodium hydroxide, platinum-rhodium oxide, or platinum on carbon, etc. Reaction conditions such as, for example, choice of solvent, reaction pressure and co-catalyst, can be varied by one skilled in the art. Alternately, other reducing agents, such as, for example, triphenylphosphine, sodium boron hydride, and lithium aluminum hydride, can be used alone to convert the azide to the amine.

Poly(trimethylene ether)glycols have chain-end hydroxyl groups that can be reacted and converted to other groups. In some embodiments, the chain-end hydroxyl groups of the poly(trimethylene ether)glycols are converted to better leaving groups for nucleophilic substitution reactions. "Better leaving groups", as used herein, means leaving groups that are better than hydroxyl groups. Leaving groups in connection with nucleophilic substitution reactions are discussed in page 352-357, March's Advanced Organic Chemistry (4$^{th}$ Edition) by Michael B. Smith and Jerry March, John Wiley and Son's Inc. Compounds having such better leaving groups include reactive esters, oxonium ions, and fluorinated compounds of the following formula:

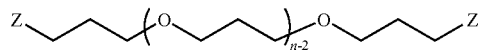

where Z is, for example: mesylate (—OMs), tosylate (—OTs), nosylate (—ONs), brosylate (—OBs), triflate (—OTf), nonaflate, tresylate, iodide (—I). Particularly preferred leaving groups include those selected from the group consisting of: —OMs (wherein Ms is methanesulfonyl), OTs (wherein, Ts is toluenesulfonyl), —ONs (wherein Ns is p-nitrobenzenesulfonyl), —OBs (wherein Bs is p-bromonenznesulfonyl), —OTf (wherein Tf is trifluoromethanesulfonyl), nonaflate (nonafluorobutanesulfonate), and tresylate (2,2,2-trifluoroethanesulfonate). One embodiment of the process includes contacting poly(trimethylene ether)glycol with halides or anhydrides of the acid comprising the better living groups such as those recited hereinabove, and a base, in the presence of a solvent that is compatible with poly(trimethylene ether)glycol, such as dichloromethane or toluene, at a temperature of 0° C. or lower (typically from about −78° C. to 0° C., and more preferably from about −20° C. to 0° C.) under an inert atmosphere, such as, for example nitrogen or argon. Suitable bases include, for example, either inorganic base such as sodium hydroxide, potassium hydroxide, sodium (bi)carbonate, potassium (bi)carbonate, or organic base, such as trimethylamine, triethylamine, di-isopropylethylamine, and pyridine. After the reaction of poly(trimethylene ether)glycol with the acid halides or acid anhydrides is completed, the reaction mixture is optionally neutralized, for example, with a dilute acid such as HCl, HOAc, $H_2SO_4$, $HNO_3$, or with an ion exchange resin, then optionally filtered, and optionally further purified by extraction with solvents, such as ether, dichloromethane, chloroform, ethyl acetate, to provide poly(trimethylene ether) compounds of the following chemical structures:

ylformamide (DMF), dimethylsulfoxide (DMSO), N,N'-dimethylacetamide (DMAc), N-methylpyrrolidone (NMP), and mixtures thereof.

The abovementioned chain-end iodide functionalized poly(trimethylene ether) compound can also be synthesized by direct iodination of poly(trimethylene ether)glycol whereby the chain end hydroxyl groups are converted to iodide groups. A variety of reagents can be used, such as, for example, $BF_3$-$Et_2O$/NaI, $I_2$, $MgI_2$, triphenylphosphine/iodine/ImH. as disclosed, for example, in Hajipour et al (Tetrahedron Letters, 2006, 47, 4191-4196) as well as Reference 5-18 referenced therein.

The poly(trimethylene ether) compound, comprising a better leaving group Z, of formula

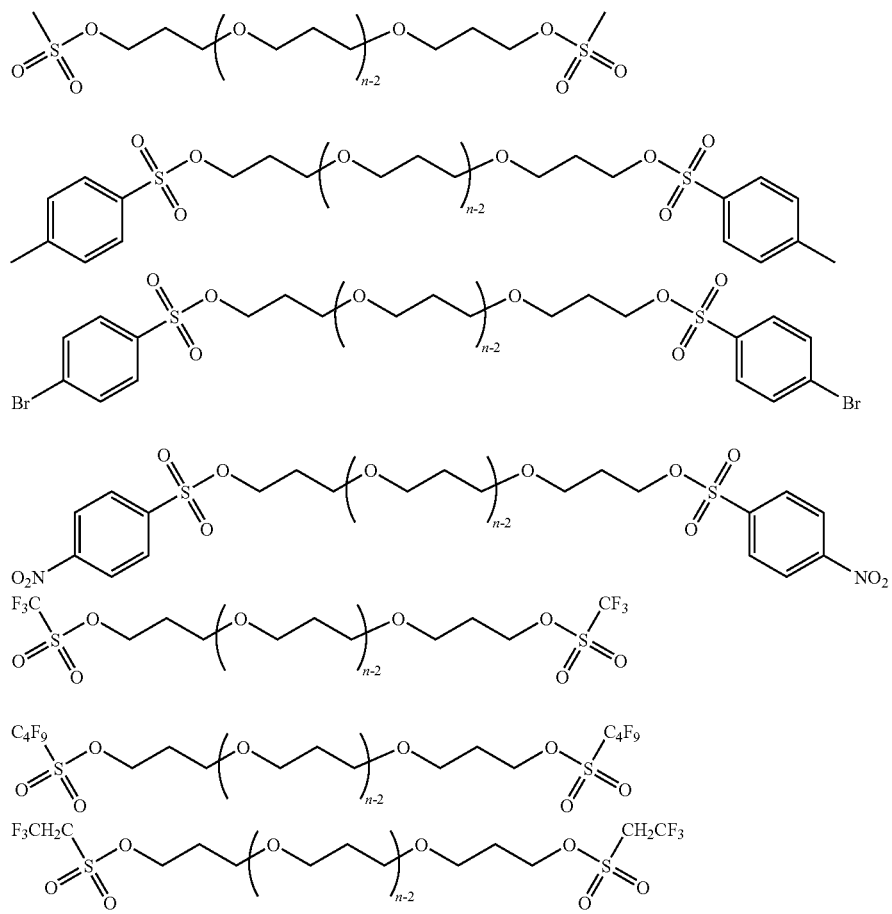

Other compounds having preferred leaving groups include iodides (—I) of formula

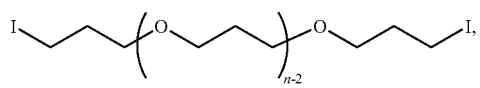

which can be prepared by further treatment of the chain-end chloride or bromide functionalized poly(trimethylene ether) compounds with an iodide source, such as sodium iodide or potassium iodide, in the presence of polar solvents, such as water, acetone, methanol, isopropanol, N,N'-dimeth-

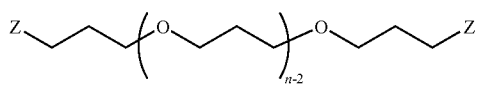

where Z is, for example: mesylate (—OMs), tosylate (—OTs), nosylate (—ONs), brosylate (—OBs), triflate (—OTf), nonaflate, tresylate, or iodide (—I) is then combined with sufficient amount of azide source to achieve the desired degree of azide functional group conversion, typically an alkali metal azide, such as sodium azide, in the presence of a solvent (typically polar solvents and alcohol solvents) at elevated temperature (25 to 200° C., and more typically 50 to 150° C.) under a pressure of 15 to 150 psi, or under atmospheric pressure, to form poly(trimethylene ether)azide of the formula

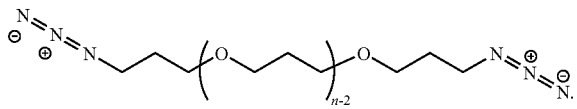

The poly(trimethylene ether)azide is then exposed to a reducing agent, such as a catalyst in the presence of hydrogen gas, at elevated pressure (15 to 500 psi, typically 20 to 100 psi) and at ambient temperature, whereby the desired poly(trimethylene ether)amine is formed. Useful reducing agents include catalysts such as metal catalysts selected from the group consisting of: Pt, Pd, $PtO_2$, Pd/C, and Raney nickel; triphenylphosphine; lithium aluminum hydride; borohydrides selected from the group consisting of: sodium borohydride, zinc borohydride, and lithium aminoborohydride wherein the amine is selected from the group consisting of diethylamine, diisopropylamine, pyrrolidine, piperidine, and morpholine; metal and metal salts selected from the group consisting of zinc and tin (II) chloride; and ammonium formate. Preferred reaction solvents are polar aprotic solvents such as N,N-dimethylformamide or N,N-dimethylacetamide, or alcohol solvents such as methanol, ethanol, and isopropanol. The catalyst is preferably dispersed on charcoal or silica. The catalyst and/or other remaining reducing agents are desirably removed after the reducing step is complete.

In another embodiment, poly(trimethylene ether)glycol is reacted with thionyl halide optionally containing a catalytic amount of dimethylformamide in the presence of a solvent to form the dihalide as described above, which is then dissolved in a mixture of aqueous ammonia and an appropriate solvent under elevated pressure (15-500 psi) and at elevated temperature (25 to 150° C., preferably 40 to 100° C.) to form the desired poly(trimethylene ether)diamine. An appropriate solvent is one that preferably does not react with ammonia and allows for the solubilization of poly(trimethylene ether) intermediate. Suitable solvents include, for example, alcohol solvents, polar aprotic solvents, and toluene.

In still another embodiment, poly(trimethylene ether)glycol is reacted with thionyl halide optionally containing a stoichiometric amount, preferably a catalytic amount, of dimethylformamide in the presence of a solvent to form the dihalide as described above, which is then exposed to anhydrous ammonia under elevated pressure (15 to 500 psi) and at elevated temperature (25 to 150° C., preferably 40-100° C.) to form the desired poly(trimethylene ether)diamine. The solvent preferably does not react with ammonia and allows for the solubilization of poly(trimethylene ether) intermediate. Suitable solvents include alcohol solvents, polar aprotic solvents, and toluene.

In yet another embodiment, the chain end hydroxyl groups are converted to better leaving groups. Especially preferred better leaving groups include those selected from the group consisting of: —OMs (wherein Ms is methanesulfonyl), —OTs (wherein Ts is toluenesulfonyl), —OTf (wherein Tf is trifluoromethanesulfonyl), tresylate (2,2,2-trifluoroethanesulfonate), and —I. The product can then be dissolved in a mixture of aqueous ammonia and an appropriate solvent under elevated pressure (15-500 psi) and at ambient or elevated temperature (25 to 150° C., preferably 25 to 80° C.) to form the desired poly(trimethylene ether)diamine. The solvent preferably does not react with ammonia and allows for the solubilization of poly(trimethylene ether) intermediate. Suitable solvents include alcohol solvents, polar aprotic solvents, and toluene.

In still another embodiment, the product formed by the reaction of the poly(trimethylene ether)glycol and better leaving group as described above is exposed to anhydrous ammonia under elevated pressure (15 to 500 psi) and at elevated temperature (25 to 150° C., preferably 25 to 80° C.) to form the desired poly(trimethylene ether)diamine. The solvent preferably does not react with ammonia and allows for the solubilization of poly(trimethylene ether) intermediate. Suitable solvents include alcohol solvents, polar aprotic solvents, and toluene.

In still another embodiment, the chain end hydroxyl groups of poly(trimethylene ether)glycol are converted to nitrile groups by cyanoethylation reaction to form a nitrile-terminated poly(trimethylene ether) of formula

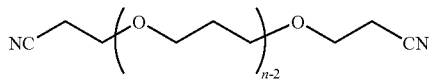

Cyanoethylation reaction is typically performed with acrylonitrile in the presence of catalytic amount of base, such as sodium hydroxide or potassium hydroxide, and ppm level of radical inhibitor, such as, for example, monomethyl ether hydriquinone (MEHQ), butylated hydroxyl toluene (BHT). A process for cyanoethylation is disclosed, for example, in Harper et al in Kirk-Othmer Encyclopedia of Chemical Technology, $3^{rd}$ Ed, 1979, volume 7, page 370-385 as well as the references cited in Harper et al.

The nitrile terminated poly(trimethylene ether) compound is then reduced to form the amine-terminated poly(trimethylene ether) compound of formula

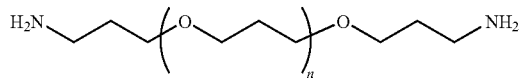

Typical reaction conditions for reducing nitriles to amines are described in detail by de Bellefon et al in Catalysis Reviews, Science and Engineering, 1994, volume 36, issue 3, page 459-506 as well as the references cited in de Bellefon et al. Suitable solvents for this reaction include: water, alcohol solvents (for example, methanol, ethanol, and isopropanol), ether solvents (for example, THF, dioxane), aromatic solvents (for example, benzene and toluene), hydrocarbon solvents (for example, hexane and octane), or mixtures thereof. A variety of catalysts can be used for this reaction including cobalt-nickel, cobalt manganese, cobalt boride, copper cobalt, iron oxide, Raney nickel, rhodium on charcoal or alumina, rhodium hydroxide, platinum-rhodium oxide, palladium or platinum on carbon, etc. The amount of catalyst is generally 0.01% to 15% by weight, preferably 0.1% to 10% by weight. The reaction temperature is generally from 50 to 250° C., more typically from 80 to 150° C. The reaction pressure is generally from 80 to 4000 psi, more typically from 150 to 1500 psi. Additives, including base, acid, or acid anhydride, can be desirably used to minimize the formation of secondary and tertiary amines. Examples include ammonia, hydroxide, hydrogen chloride, and acetic anhydride. The reaction conditions can be varied, such as by choice of solvent, reaction pressure and co-catalyst, by one skilled in the art.

The poly(trimethylene ether)diamines produced by the processes described herein can be purified by any convenient method known to those skilled in the art. Particularly useful methods include washing and extracting with solvents, passing the material through one or more ion exchange columns, or subjecting the diamines to dialysis against solvents using dialysis apparatus comprising separation membranes, or treating with activated carbon, or a combination of the above. Suitable solvents for purification are solvents that are compatible with the poly(trimethylene ether)diamines, such as, for example, hexane, heptane, toluene, xylenes, dichloromethane, chloroform, isopropanol, ethanol, methanol, ethylene glycol, propylene glycol, water, ether, tetrahydrofuran, dioxane, acetonitrile, acetone, ethyl acetate, N,N'-dimethylformamide (DMF), dimethylsulfoxide (DMSO), N,N'-dimethylacetamide (DMAc), N-methylpyrrolidone (NMP) and mixtures thereof.

The processes described herein use poly(trimethylene ether)glycol (PO3G), as a starting component to make the linear diamine moieties. As the term PO3G is used herein, it represents an oligomeric or polymeric ether glycol in which at least 50% of the repeating units are trimethylene ether units. More preferably from about 75% to 100%, still more preferably from about 90% to 100%, and even more preferably from about 99% to 100%, of the repeating units are trimethylene ether units.

PO3G is preferably prepared by polycondensation of monomers comprising 1,3-propanediol, preferably in the presence of an acid catalyst, thus resulting in polymers or copolymers containing —(CH$_2$CH$_2$CH$_2$O)— linkage (e.g, trimethylene ether repeating units). As indicated above, at least 50% of the repeating units are trimethylene ether units. A preferred source of 1,3-propanediol is via a fermentation process using a renewable biological source. As an illustrative example of a starting material from a renewable source, biochemical routes to 1,3-propanediol (PDO) have been described that utilize feedstocks produced from biological and renewable resources such as corn feed stock.

In addition to the trimethylene ether units, lesser amounts of other units, such as other polyalkylene ether repeating units, may be present. In the context of this disclosure, the term "poly(trimethylene ether)glycol" encompasses PO3G made from substantially pure 1,3-propanediol, as well as those oligomers and polymers (including those described below) containing up to about 50% by weight of comonomers.

PO3G can be made via a number of processes known in the art, such as processes disclosed in U.S. Pat. No. 7,161,045 and U.S. Pat. No. 7,164,046.

As indicated above, PO3G may contain lesser amounts of other polyalkylene ether repeating units in addition to the trimethylene ether units. The monomers for use in preparing poly(trimethylene ether)glycol can, therefore, contain up to 50% by weight (preferably about 20 wt % or less, more preferably about 10 wt % or less, and still more preferably about 2 wt % or less), of comonomer polyols in addition to the 1,3-propanediol reactant. Comonomer polyols that are suitable for use in the process for making the PO3G include aliphatic diols, for example, ethylene glycol, 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol; cycloaliphatic diols, for example, 1,4-cyclohexanediol, 1,4-cyclohexanedimethanol and isosorbide; and polyhydroxy compounds, for example, glycerol, trimethylolpropane, and pentaerythritol. A preferred group of comonomer diols is selected from the group consisting of ethylene glycol, 2-methyl-1,3-propanediol, 2,2-dimethyl-1,3-propanediol, 2,2-diethyl-1,3-propanediol, 2-ethyl-2-(hydroxymethyl)-1,3-propanediol, C$_6$-C$_{10}$ diols (such as 1,6-hexanediol, 1,8-octanediol and 1,10-decanediol) and isosorbide, and mixtures thereof. A particularly preferred diol other than 1,3-propanediol is ethylene glycol, and C$_6$-C$_{10}$ diols can be particularly useful as well.

One preferred PO3G that contains comonomer is poly (trimethylene-ethylene ether)glycol. Preferred poly(trimethylene-ethylene ether)glycols are prepared by acid catalyzed polycondensation of from 50 to about 99 mole % (preferably from about 60 to about 98 mole %, and more preferably from about 70 to about 98 mole %) 1,3-propanediol and up to 50 to about 1 mole % (preferably from about 40 to about 2 mole %, and more preferably from about 30 to about 2 mole %) ethylene glycol.

Preferably the PO3G has an Mn (number average molecular weight) of at least about 250, more preferably at least about 500, and still more preferably at least about 1000. The Mn is preferably less than about 10000, more preferably less than about 5000, and still more preferably less than about 2500. Blends of PO3Gs can also be used. For example, the PO3G can comprise a blend of a higher and a lower molecular weight PO3G, preferably wherein the higher molecular weight PO3G has a number average molecular weight of from about 1000 to about 5000, and the lower molecular weight PO3G has a number average molecular weight of from about 200 to about 950. The Mn of the blended PO3G will preferably still be in the ranges mentioned above.

Preferred PO3G is polydisperse, having a polydispersity (i.e. Mw/Mn) of preferably from about 1.0 to about 2.2, more preferably from about 1.2 to about 2.2, and still more preferably from about 1.5 to about 2.1. The polydispersity can be adjusted by using blends of PO3G.

The functionalized polyamines disclosed herein are suitable for use in a variety of applications including as chain extenders for polyurethane urea polymers, curing agents for epoxy resins, polyurethane coatings, components for making polyamides, initiators for the preparation of polyols, and health care product additives.

EXAMPLES

DSC measurements were performed on a TA Instruments Q2000. Samples were allowed to undergo heating, cooling, and re-heating cycle from −90° C. to 100° C. at a rate of 10° C./min under nitrogen. TGA measurements were performed on a TA Instruments Q500. Samples were heated from RT to 500° C. at a rate of 5° C./min under nitrogen.

Example 1

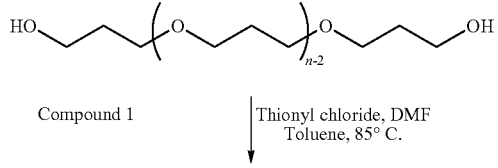

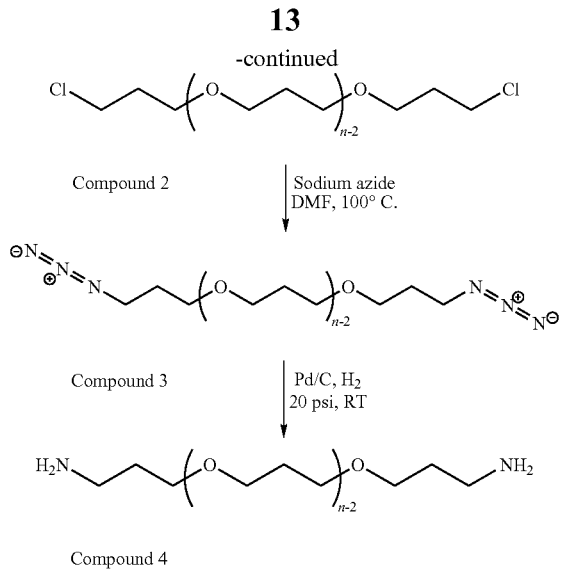

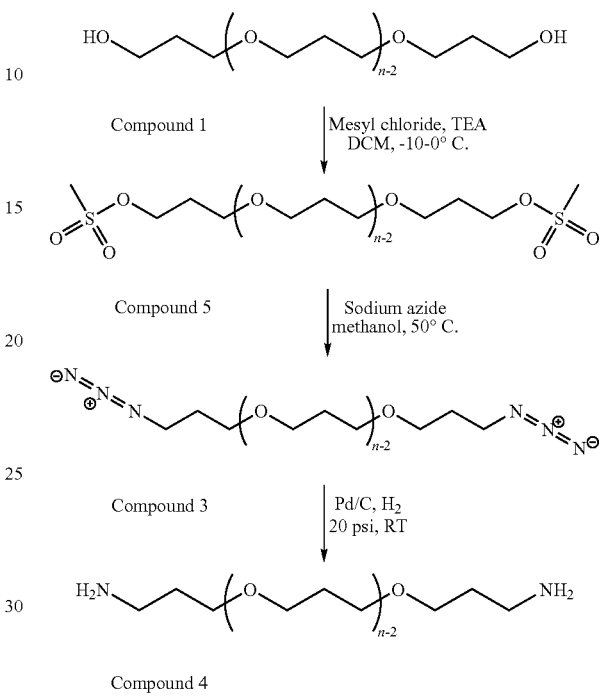

Poly(trimethylene ether)glycol (Compound 1) (50.0 g, $M_{n,NMR}$=652 g/mol, $M_{n,SEC}$=699 g/mol, PDI=1.44), was dissolved in toluene (150 mL) and DMF (0.237 mL). The solution mixture was cooled down to 0° C. To this was added toluene (50 mL) solution of thionyl chloride (73.1 g, 44.8 mL) slowly over 1.5 hour. The mixture was allowed to stir at 0° C. for 1 hour, at ambient temperature (approximately 25° C.) for 30 min, and at 85° C. for 3 hours. Excess thionyl chloride was removed under vacuum. The crude was re-suspended in methylene chloride (150 mL) with neutral alumina, filtered, and concentrated to obtain Compound 2 (49.0 g): $^1$H NMR (CDCl$_3$, 500 MHz) δ 3.63 (t, J=6.5 Hz, 4H), 3.54 (t, J=6.1 Hz, 4H), 3.48 (m, ~34H), 2.01 (quint, J=6.2 Hz, 4H), 1.82 (m, ~17H); $^{13}$C NMR (CDCl$_3$, 500 MHz) δ 68.62, 68.53, 68.37, 67.80, 42.60, 33.44, 30.78, 30.73; IR: 2804-2949, 1489, 1452, 1375, 1300, 1256, 1117, 927, 660 cm$^{-1}$; SEC: $M_n$=684 g/mol, PDI=1.41; IV: 0.043 mL/g; $T_g$: −86° C.; $T_c$: −50° C.; $T_m$: −7, 4° C.; $T_{50}$: 204° C. (temperature of 50% weight loss based on TGA data). The DSC measurements were performed on a TA Instruments Q2000. Samples were allowed to undergo heating, cooling, and re-heating cycle from −90° C. to 100° C. at a rate of 10° C./min under nitrogen. TGA measurements were performed on a TA Instruments Q500. Samples were heated from RT to 500° C. at a rate of 5° C./min under nitrogen.

Compound 2 (40.0 g) was dissolved in DMF (200 mL) followed by addition of sodium azide (30.2 g). The reaction mixture was heated to 100° C. for 4 hours under nitrogen. The reaction mixture was filtered and the filtrate was concentrated to obtain Compound 3 in quantitative yield: $^1$H NMR (DMSO-d$_6$, 500 MHz) δ 3.39 (m, ~42H), 1.75 (quint, J=6.5 Hz, 4H), 1.69 (m, ~17H); $^{13}$C NMR (DMSO-d$_6$, 500 MHz) δ 67.52, 67.43, 67.39, 67.27, 48.34, 30.34, 29.98, 28.97; IR: 3518 (DMF), 2803-2949, 2096, 2063 (DMF), 1665 (DMF), 1489, 1446, 1373, 1280, 1115, 941, 779 cm$^{-1}$; SEC: $M_n$=701 g/mol, PDI=1.38.

To a pressure vessel (100 mL) was added an ethanol (10 mL) solution of Compound 3 (4.0 g), followed by the addition of palladium (10 wt. % on activated carbon, 0.24 g). The solution mixture was place under hydrogen (20 psi) at ambient temperature (approximately 25° C.) overnight. The reaction mixture was filtered and concentrated to provide Compound 4: $^1$H NMR (DMSO-d$_6$, 500 MHz) δ 3.38 (m, ~42H), 2.57 (t, J=6.8 Hz, 4H), 1.69 (m, ~20H), 1.55 (t, J=6.7 Hz, 4H); IR: 3580 (DMF), 3392, 3318, 2804-2947, 2056 (DMF), 1682 (DMF), 1627, 1489, 1445, 1371, 1328, 1256, 1115, 933, 771 cm$^{-1}$; SEC: $M_n$=701 g/mol, PDI=1.38.

Example 2

Poly(trimethylene ether)glycol (Compound 1) (80.0 g) was combined with triethylamine (50.8 mL) and dichloromethane (DCM) (800 mL). The reaction mixture was cooled down to −10° C. with stirring under nitrogen. To this was added DCM (400 mL) solution of mesyl chloride (23.7 mL) slowly. After 40 min, the reaction mixture was filtered and the filtrate was washed with dilute HCl (0.5 M). The combined organic layer was washed with sodium bicarbonate solution (8 wt. %), DI water, dried with MgSO$_4$, filtered, and concentrated to provide Compound 5 (90.9 g): $^1$H NMR (CDCl$_3$, 500 MHz) δ 4.33 (t, J=6.3 Hz, 4H), 3.52 (t, J=5.9 Hz, 4H), 3.48 (m, ~36H), 3.00 (s, 6H), 2.00 (quint, J=6.1 Hz, 4H), 1.82 (m, ~18H); $^{13}$C NMR (CDCl$_3$, 500 MHz) δ 68.60, 68.28, 68.24, 68.06, 66.46, 37.60, 30.52, 30.43, 29.94; IR: 2810-2957, 1487, 1445, 1358, 1265, 1177, 1115, 980, 951, 845, 530 cm$^{-1}$.

Compound 5 (10.0 g) was dissolved in methanol (40 mL) followed by addition of sodium azide (4.83 g). The reaction mixture was heated to 50-55° C. for 36 hours under nitrogen. The reaction mixture was filtered and the filtrate was concentrated to obtain Compound 3 (9.2 g): $^1$H NMR (CDCl$_3$, 500 MHz) δ 3.48 (m, ~42H), 3.38 (t, J=6.7 Hz, 4H), 1.82 (m, ~23H); $^{13}$C NMR (CDCl$_3$, 500 MHz) δ 68.08, 68.00, 67.83, 67.47, 30.22, 30.16, 29.62; IR: 2804-2949, 2099, 1486, 1439, 1373, 1304, 1265, 1117, 943, 777 cm$^{-1}$; SEC: $M_n$=675 g/mol, PDI=1.44; $T_g$: <−100° C.; $T_c$: −63° C.; $T_m$: −9, 5° C.; $T_{50}$: 354° C.

Compound 3 was converted to Compound 4 under similar condition described in Example 1: $^1$H NMR (CDCl$_3$, 500 MHz) δ 3.48 (m, ~42H), 2.79 (t, J=6.8 Hz, 4H), 1.82 (m, ~19H), 1.71 (quint, J=1.71 Hz, 4H), 1.19 (br s, 4H); $^{13}$C NMR (CDCl$_3$, 500 MHz) δ 69.42, 68.29, 67.96, 39.82, 33.73, 30.36, 30.22; IR: 3397, 3337, 2806-2947, 1628, 1487, 1485, 1444, 1373, 1117, 934, 835 cm$^{-1}$; $T_g$: −83° C.; $T_c$: −48° C.; $T_m$: −5, 7, 10° C.; $T_{50}$: 345° C.

isopropanol followed by treatment with ion exchange resin or by dialysis to provide Compound 4 in its free amine form.

Example 3

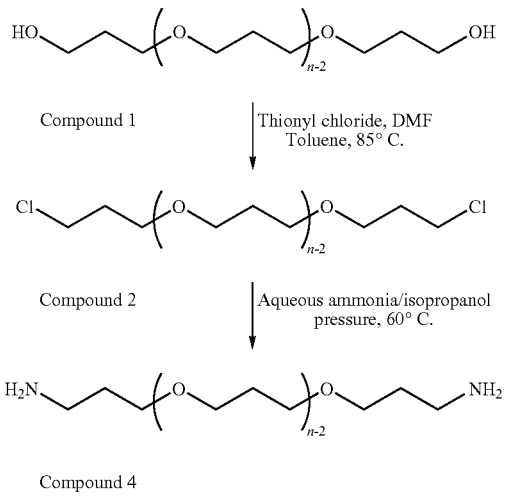

Compound 2 is dissolved in a mixture of aqueous ammonia/isopropanol. The reaction mixture is placed in a pressure vessel and heated to 60° C. After the reaction is complete, solvents and reagents are removed under vacuum. Compound 4 is prepared in its free amine form after treatment with ion exchange resin or by dialysis.

Example 4

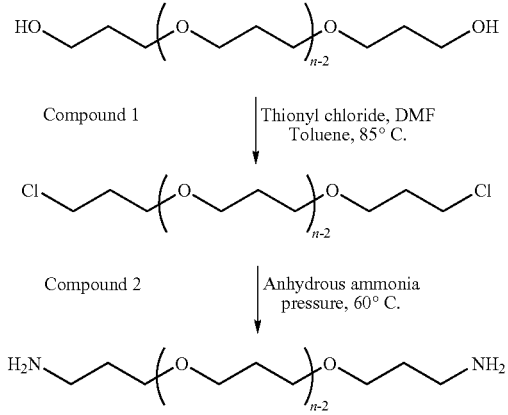

Compound 2 and anhydrous ammonia are combined in a sealed pressure vessel. The reaction mixture is heated to 60° C. The crude material is dissolved in a mixture of water and

Example 5

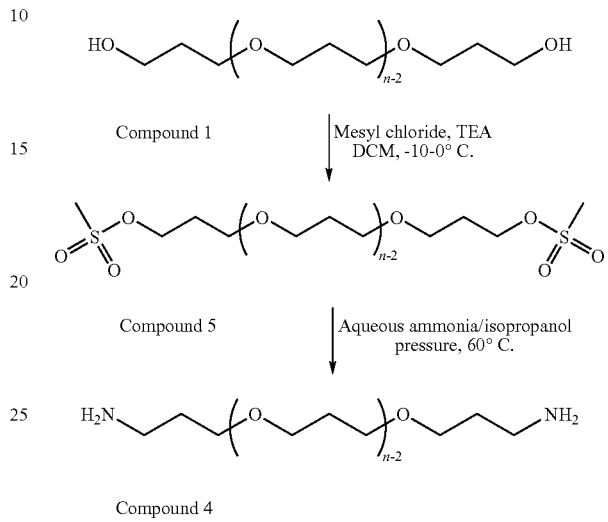

Compound 5 is dissolved in a mixture of aqueous ammonia/isopropanol. The reaction mixture is placed in a pressure vessel and heated to 60° C. After the reaction is complete, solvents and reagents are removed under vacuum. Compound 4 is prepared in its free amine form after treatment with ion exchange resin or by dialysis.

Example 6

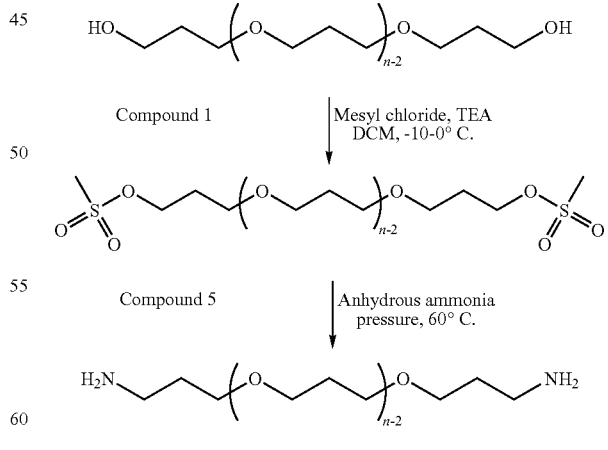

Compound 5 and anhydrous ammonia are combined in a sealed pressure vessel. The reaction mixture is heated to 60° C. The crude material is dissolved in a mixture of water and isopropanol followed by treatment with ion exchange resin or by dialysis to provide Compound 4 in its free amine form.

Example 7

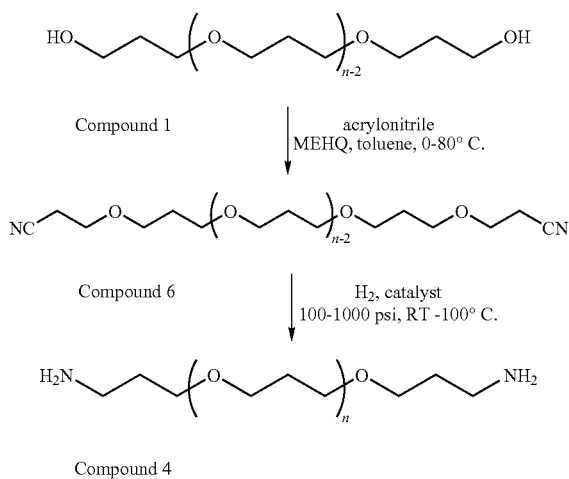

Compound 1 is combined with catalytic amount of sodium hydroxide and radical inhibitor monomethyl ether hydroquinone (MEHQ) (10-100 ppm) in a appropriate solvent such as toluene, dioxane, THF. Acrylonitrile (2-10 equiv. to the OH groups in Compound 1) is then added slowly to the solution mixture with proper cooling at 0-20° C. to avoid over heat due to the exothermic reaction. The reaction mixture is heated at 30-80° C. to complete conversion. The reaction mixture is then cooled to room temperature and quenched by dropwise addition of acetic acid. Solvent as well as the unreacted acrylonitrile are evaporated under vacuum and the reaction mixture was partitioned between methylene chloride and water. The organic layer is water washed, dried, and concentrated to provide Compound 6. Crude Compound 6 is optionally further purified before reduction.

Compound 6 is dissolved in methanol saturated with ammonia, followed by the addition of catalytic amounts of Raney nickel. The solution mixture is placed under hydrogen (150 psi) at RT overnight. Catalyst is filtered and the reaction mixture is concentrated to provide Compound 4.

What is claimed is:

1. A poly(trimethylene ether) diamine of the formula

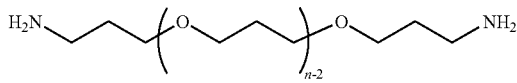

wherein n is 19-88.

2. The poly(trimethylene ether) diamine of claim 1, wherein the poly(trimethylene ether) amine is formed from a poly(trimethylene ether) glycol obtained from the polycondensation of biologically-derived 1,3-propane diol.

3. A process for making a poly(trimethylene ether) diamine of the formula

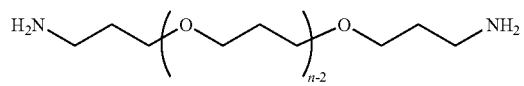

comprising:
a) converting the chain-end hydroxyl groups of poly(trimethylene ether) glycol of the formula

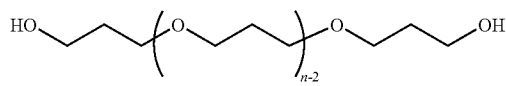

to better leaving groups to form a compound of formula

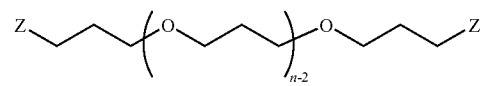

where Z is selected from the group consisting of mesylate (—OMs), tosylate (—OTs), nosylate (—ONs), brosylate (—OBs), triflate (—OTf), nonaflate, tresylate and iodide (—I);
b) combining the compound of step (a) with anhydrous ammonia, or a mixture of aqueous ammonia and a solvent, under a pressure of about 15 to 500 psi at a temperature of 25 to 150° C. to form a poly(trimethylene ether) diamine of the formula

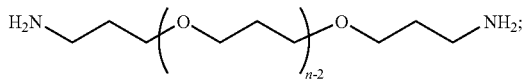

wherein n is 19-88.

4. A process for making a poly(trimethylene ether) diamine of the formula

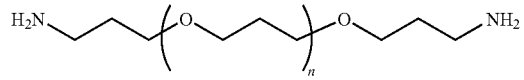

comprising:
a) converting the chain-end hydroxyl groups of poly(trimethylene ether) glycol of the formula

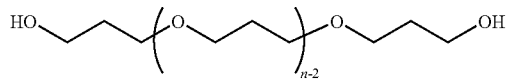

to nitrile groups to form a nitrile-terminated poly(trimethylene ether) of formula

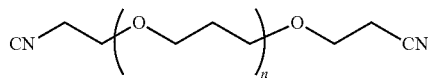

b) reducing the nitrile-terminated poly(trimethylene ether) in the presence of hydrogen and catalyst at a temperature of 50 to 250° C. under pressure of 80 to 4000 psi to form a poly(trimethylene ether) diamine of the formula

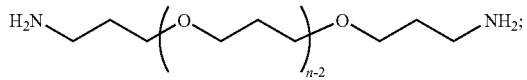

wherein n is 19-88.

5. The process of claim 3 or 4, wherein the poly(trimethylene ether) glycol is biologically derived.

6. The process of claim 5, further comprising purifying the poly(trimethylene ether) diamine.

7. The process of claim 6, wherein the purifying comprises a process selected from the group consisting of:
(a) treating the poly(trimethylene ether) diamine by washing and extracting with solvents;
(b) treating the poly(trimethylene ether) diamine by passing through one or more ion exchange columns;
(c) treating the poly(trimethylene ether) diamine by dialysis through membranes against solvent;
(d) treating the poly(trimethylene ether) diamine with activated carbon;
(e) treating the poly(trimethylene ether) diamine using a combination of steps (a) through (d).

* * * * *